United States Patent [19]

Panzer

[11] 4,449,521
[45] May 22, 1984

[54] SEXUAL AID

[76] Inventor: Jack S. Panzer, 12930 Denmark, Detroit, Mich. 48217

[21] Appl. No.: 430,996

[22] Filed: Sep. 30, 1982

Related U.S. Application Data

[63] Continuation-in-part of Ser. No. 300,301, Sep. 11, 1981, abandoned.

[51] Int. Cl.³ ............................................. A61F 5/00
[52] U.S. Cl. .................................................. 128/79
[58] Field of Search ........................................ 128/79

[56] References Cited

U.S. PATENT DOCUMENTS

| | | | |
|---|---|---|---|
| 853,410 | 5/1907 | Huebner | 128/79 |
| 3,920,007 | 11/1975 | Line | 128/79 |

FOREIGN PATENT DOCUMENTS

| | | | |
|---|---|---|---|
| 142022 | 6/1935 | Austria | 128/79 |
| 183924 | 4/1907 | Fed. Rep. of Germany | 128/79 |
| 884357 | 12/1961 | United Kingdom | 128/79 |

*Primary Examiner*—Dalton L. Truluck
*Attorney, Agent, or Firm*—Gifford, VanOphem, Sheridan, Sprinkle & Nabozny

[57] ABSTRACT

A genital splint permitting a male to achieve penetration during sexual intercourse comprises a base adjacent the torso, an adjustable collar compressingly engaging the glans of the penis, and adjustable support column means for maintaining the collar in an adjustable yet fixed position relative to the base. Preferably, a pliable material such as silicon tubing covers each of these elements for comfort and to prevent damage to body tissues during intercourse. Adjustment of the length of the support column means occurs by either the telescopic or the threaded engagement of an inner rod and an outer tube, the rod and tube each being attached to one of the collar and the base.

7 Claims, 6 Drawing Figures

SEXUAL AID

CROSS-REFERENCE TO RELATED APPLICATION

This application is a continuation-in-part of Applicant's co-pending U.S. Ser. No. 300,301, filed Sept. 11, 1981 now abandoned.

FIELD OF THE INVENTION

The present invention relates generally to medical applicances and, more particularly, to a genital splint to permit a male to achieve penetration during sexual intercourse.

DESCRIPTION OF THE PRIOR ART

Normal male-female sexual relations are often hindered by the failure of a male to obtain or maintain a satisfactory erection of the penis. Regardless of whether the problem is psychological or physiological, penetration may be impossible unless some form of sexual aid is used. One convenient type of sexual aid comprises a splint type structure which stretches the penis and supports it outwardly from the body.

One such device which is previously known is found in U.S. Pat. No. 3,920,007 to Line, owned by the applicant herein. The sexual aid of Line includes a ring-like base which slideably receives the penis therethrough. A rigid support column extends perpendicularly to the ring-like base and includes a collar adapted for engagement with the corona of the glans of the penis, whereby the penis is supported in an extended position outwardly from the body as the collar compressingly engages the glans.

Another such device is found in applicant's own U.S. patent application Ser. No. 300,301, filed Sept. 11, 1981. The sexual aid therein includes a split ring base, an elongated support column extending perpendicularly to the base, a support collar, and a pliable coating covering each of these elements of the sexual aid. The split-ring type base therein permits the base to engage and expand with the penis throughout various stages of erection of the penis. Additionally, the collar is formed so that no relatively sharp ends of the collar can become exposed when the glans supporting tube becomes displaced from the collar; rather, upon such displacement, only a pliant coating is exposed. Such a coating applied to the column and split-ring base renders the device much more suitable for comfortable and undamaging contact with body tissues during sexual relations.

While applicant's device in the aforesaid Ser. No. 300,301 functioned and continues to function admirably for its intended purpose, the device is disadvantageous in that manufacture or assembly of the device could take place only after the penile dimension of the individual patient was known, because of the variations in penile thickness and length in individuals. Thus, the device did not result in the optimum use of either time or cost in supplying a particular individual with the device.

SUMMARY OF THE PRESENT INVENTION

The present invention overcomes the above-mentioned disadvantages by providing a sexual aid comprising an elongated and adjustable support column means extending perpendicularly from a base to a support collar for maintaining the collar in an adjustable yet fixed position relative to the base. Preferably, a pliable material covers each of these elements of the sexual aid. The preferred embodiment of the invention retains the advantages provided in applicant's aforesaid application Ser. No. 300,301: the split-ring type base permits the base to engage and expand with the penis throughout various stages of erection; the collar is formed so that no relatively sharp ends of the collar become exposed when the glans supporting tube becomes displaced from the collar; and with the material applied to the collar, the adjustable support column means and the split-ring base, the device is much more suitable for comfortable and undamaging contact with body tissues during sexual relations. The use of an adjustable support column and an adjustable collar provides additional advantages in permitting a better fit of the device to a particular patient and in better retaining the device on the penis during use. The adjustable device described herein permits manufacture of the component parts of the device which do not have to be sized to the individual prior to manufacture or sale.

BRIEF DESCRIPTION OF THE DRAWING

The present invention will be better understood by reference to the following detailed description when read in conjunction with the accompanying drawing, wherein like reference characters refer to like parts throughout the several views, and in which.

DETAILED DESCRIPTION OF THE PREFERRED EMBODIMENT OF THE PRESENT INVENTION

Figure 1:
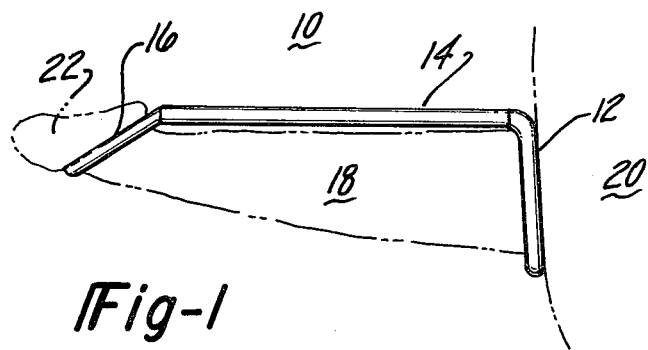
FIG. 1 is a side plan view of the preferred embodiment of the present invention.

With reference now to FIG. 1, a sexual aid 10 in accordance with the present invention is thereshown comprising a base portion 12, a support collar 16, and an adjustable, rigid support column means 14 for maintaining the base 12 and the support collar 16 in a fixed position relative to one another. The base 12 is a split-ring and extends around a penis 18 and rests against a torso 20 adjacent to the root of the penis 18. The collar 16 engages the glans 22 of the penis at a position spaced outwardly from the torso 20.

Figures 2, 4, 5:
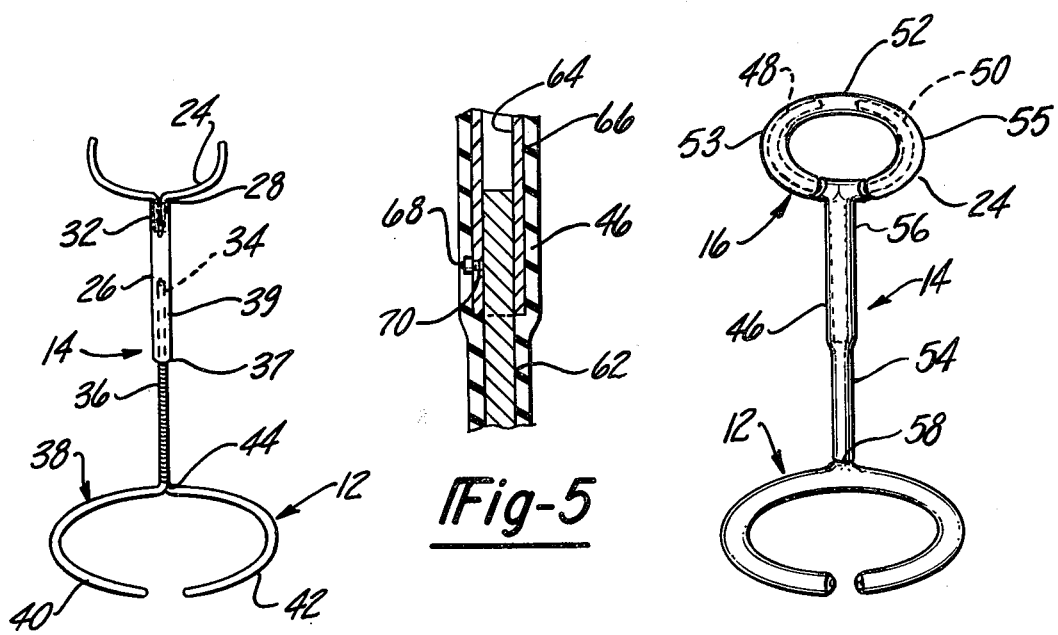
FIG. 2 is a perspective view of the embodiment shown in FIG. 1 with portions removed for clarity.
FIG. 4 is a perspective view of the preferred embodiment of the present invention.
FIG. 5 is a cross-sectional view of a portion of another preferred embodiment of the present invention.
Figure 3:
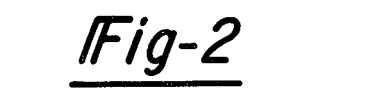
FIG. 3 is a cross-sectional view of a portion of the preferred embodiment of the present invention.

Referring now to FIGS. 2 and 3, the column means 14 is thereshown and comprises a threaded rod 36 disposed within a hollow and matchingly threaded tube 26. As can best be seen in FIG. 2, an arcuate member 24 is attached to one end 32 of the tube 26 by insertion of depending arms 28 into the one end 32 of the tube 26, and fixing the arms therein by crimping the one end 32 around the arms 28. Preferably, the arcuate member 24 comprises 0.037 inch spring wire so as to provide the optimum combination of flexibility and resistance to deformation of the arcuate member during use of the device 10, when the dimension of the collar 16 is changed.

One end 34 of the rod 36 is threadably received through another open end 37 of the tube 26 (FIG. 3). On an opposite end 38 of the rod 36 is formed a first portion 40 (FIG. 2) of the split-ring base 12. A second portion 42 of the split-ring base 12 is attached to the rod 36 by any convenient means, such as by a weld 44.

Referring now to FIG. 4, the present invention is thereshown wherein the base 12 and the arcuate member 24 of FIG. 2 have been covered with Teflon tubing, the base 12 and the support column 14 then being covered with a pliant plastic material 46, such as silicon tubing. (Teflon is a registered trademark of E. I. DuPont de Nemours Co., for tetra fluoroethylene polymers.) A tubular section 54 of the material 46 has a fixed end 56 adjacent the collar 16, and further has a free end 58 which is disposed adjacent the base 12 but is adjustable in position along the support column means 14. Assembly of the device 10 is completed by slidably engaging one end 53 of a segment of flexible silicon tube 52 over one Teflon-coated free end 48 of the arcuate member 24.

The device 10 is now in condition for use as a genital splint as follows.

The tubing section 54 is pulled towards the fixed end 56 so that the free end 58 is moved away from the base collar 12. This permits free rotation of the rod 36 relative to the tube 26 so as to adjust the length of the support column means 14, as shown by arrow 60 in FIG. 4. Once the length of support column means 14 is adjusted to the penile dimension of the patient, the tubing section 54 is pushed away from the fixed end 56 so that the free end 58 is moved towards and abuts the base collar 12. This prevents rotation of the rod 36 relative to the tube 26, thereby fixing the length of the support column means 14.

Figure 4A:
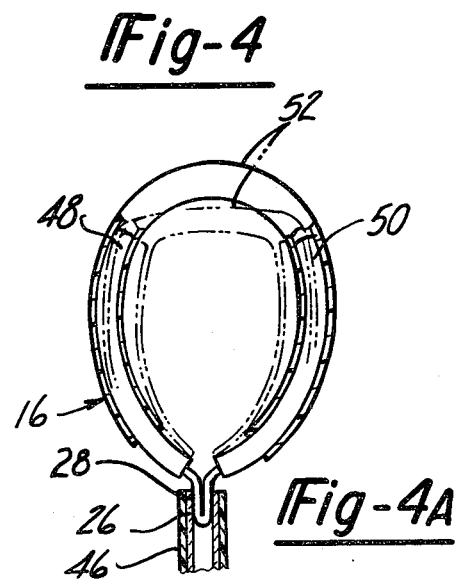
FIG. 4A is a top view of a portion of the preferred embodiment of the present invention.

The penis 18 is then inserted through the base ring 12 towards the collar 16 until the corona of the glans 22 engages the collar 16. The arcuate member 24 is adjusted to accommodate the thickness of the penis as follows. The flexible tube 52, having had the one end 53 slideably engaged with the one free end 48 of the arcuate member 24, is wrapped around the penis adjacent the glans 22, and another end 55 of the flexible tube 52 is slideably engaged over the other Teflon-coated free end 50 of the arcuate member 24, and thereby forms a complete loop around the penis. Once engaged, the other end 55 of the tube 52 is repeatedly pushed on the free end 50 of the arcuate member 24, until sufficient tension is developed in the tube 52 to snugly yet comfortably grip the penis 18. Increasing the tension in the tube 52 draws together the ends 48 and 50 of the arcuate member 24, from the position shown in solid lines in FIG. 4A to the position shown in phantom therein, and thereby tightens the grip of the collar 12 on the penis 18. Thus, the penis 18 is comfortably entrained within the collar 16 between the flexible tube 52 and the pliant plastic material 46 on the arcuate member 24. In addition, the base ring 12 is also covered with the pliant plastic material 46 and thereby comfortably engages the skin adjacent the root of the penis 18. Initially, the terminal ends of the portions 40 and 42 of the base are disposed closely adjacent to each other so that the base comfortably and circumferentially engages the penis 18. Thus, the column 14 is retained closedly adjacent to the penis.

After sexual relations have been initiated and the penis 18 begins to expand and become erect, the collar 16 and the base 12 can correspondingly expand due to the elasticity of the members 40, 42 and 52. Thus they do not restrict the growth of the penis but continue to maintain the column 12 in its position closely adjacent the penis. If the tension in the tube 52 is so great as to cause discomfort during use, such as by the collar 16 gripping the penis 18 too snugly due to expansion and erection of the penis 18, the other end 55 of the tube 52 may be pushed oppositely to the way in which it was pushed onto the free end 50 and thereby decrease the tension in the tube 52, and permit resilient separation of the free ends 48 and 50. Moreover, any looseness which might occur between the base 12 and the root of the penis does not cause discomfort for the reason that the pliant plastic material 46 cushions the contact between the device 10 and the skin tissues.

The device 10 may be removed from the penis 18 after use by removing the other end 55 of the flexible tube 52 from the free end 50 of the arcuate member 24.

Another preferred embodiment of the present invention is shown in FIG. 5 wherein a different adjustable support column means 14 is shown comprising a straight sided rod 62 which is disposed in a straight walled longitudinal bore 64 in a tube 66. The rod 62 and the tube 66 correspond in function to the rod 36 and the tube 26 in the previously described embodiment. However, adjustment of the length of the support column means 14 occurs by the telescoping of the rod 62 within the tube 66. The length of the support column means 14 is fixed by tightening of a set screw 68 disposed in a threaded lateral bore 70 in the tube 66. Adjustment of the length of the support column means 14 is possible after application of the pliant plastic material 46 by breeching or compression of the material 46 sufficiently to permit loosening and re-tightening of the set screw 68. The material 46 should be chosen to be resilient and flexible enough to permit such adjustment without tearing or ripping.

Of course, other means for fixing the length of the support column 14 besides the set screw 68 may be used as well. Once the desired length of the support column 14 is chosen, and before the pliant plastic material 46 is applied, heat melt glue (not shown) may be applied in order to fix the length of the support column 14 after telescoping of the rod 62 in the tube 66.

One particular advantage of the first described preferred embodiment is that the device may be completely manufactured prior to sale and use without need for measurement of the penile length or thickness of the individual patient, provided such patient has a penile length and thickness not substantially different from the average. For example, if the threaded rod 36 and the tube 26 are each about 2 inches long, then the support column means may vary in length from about 2 to about 4 inches, accommodating penile lengths of about 3.5 to about 7 inches. Other lengths for the rod 36 and the tube 26 may be employed if the penile length of the patient falls outside this range. Likewise bending the arcuate member 24 provides means for comfortably retaining penises of various thicknesses.

Another advantage of the first described preferred embodiment is that the patient's doctor or the patient himself may adjust the length and arcuate member 24 of the device 10 without the need of any tools, or special expertise or training. This makes the device easier for the patient to use properly than have been the previously known devices that employed columns of fixed length.

The arcuate member 24 may alternatively comprise a pair of separate arms (not shown) each having a depending leg 28 for attachment to the tube 26.

Having thus described my invention, many modifications thereto will become apparent to those skilled in the art to which it pertains without departing from the scope and spirit of the present invention as defined in the appended claims.

I claim:

1. A sexual aid for use by a human male comprising:
a base collar;
a support collar comprising an arcuate member having two free ends spaced apart from one another and a flexible tube attachable to said two free ends and forming a complete ring whereby said support collar is adjustable to accomodate penises of varying thicknesses and said flexible tube expands upon expansion of the penis;
an adjustably fixable support column means interposed between said base collar and said support collar for maintaining said base collar and said support collar in a fixed position relative to one another; and
an elastically extendable means surrounding said support column.

2. The invention as defined in claim 1 wherein said support column means comprises an inner rod and an outer tube, wherein said inner rod is threadably received within said outer tube.

3. The invention as defined in claim 1 wherein said support collar is adjusted by reversible constriction of said support collar.

4. The invention as defined in claim 1 wherein said base collar comprises a split ring.

5. The invention as defined in claim 1 wherein said base collar, said support collar, and said support column means are covered with a pliant plastic material.

6. The invention as defined in claim 5 wherein said pliant plastic material comprises silicon tubing.

7. The invention as defined in claim 1 wherein said elastically extendable means surrounding said support column is engageable with said base collar thereby fixing the length of said support column means.

* * * * *